US00PP32214P2

(12) United States Plant Patent
Hoogkamp

(10) Patent No.: US PP32,214 P2
(45) Date of Patent: Sep. 15, 2020

(54) ***CURCUMA* PLANT NAMED 'CURALIDIMP'**

(50) Latin Name: *Curcuma alismatifolia*
Varietal Denomination: Curalidimp

(71) Applicant: Timothy Johan Herman Hoogkamp, Doetinchem (NL)

(72) Inventor: Timothy Johan Herman Hoogkamp, Doetinchem (NL)

(73) Assignee: Nubilus B.V., Naaldwijk (NL)

( * ) Notice: Subject to any disclaimer, the term of this patent is extended or adjusted under 35 U.S.C. 154(b) by 0 days.

(21) Appl. No.: 16/602,489

(22) Filed: Oct. 17, 2019

(51) Int. Cl.
*A01H 5/02* (2018.01)
*A01H 6/00* (2018.01)

(52) U.S. Cl.
USPC ..... Plt./421
CPC ..... *A01H 6/00* (2018.05)

(58) Field of Classification Search
USPC ..... Plt./421
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Curcuma* plant named 'Curalidimp', characterized by its upright plant habit with slightly outwardly arching leaves; moderately vigorous to vigorous growth habit; freely clumping growth habit; relatively broad leaves; freely flowering habit; and inflorescences with bright red purple-colored upper flower bracts positioned above the foliar plane on strong and erect peduncles.

2 Drawing Sheets

Botanical designation: *Curcuma alismatifolia.*
Cultivar denomination: 'CURALIDIMP'.

BACKGROUND OF THE INVENTION

The present invention relates to a new and distinct cultivar of *Curcuma* plant, botanically known as *Curcuma alismatifolia* and hereinafter referred to by the name 'Curalidimp'.

The new *Curcuma* plant is a product of a controlled breeding program conducted by the Inventor in Naaldwijk, The Netherlands. The objective of the breeding program is to create new *Curcuma* plants that have uniform plant habit, good container performance and attractive inflorescence coloration.

The new *Curcuma* is a naturally-occurring whole plant mutation of *Curcuma alismatifolia* 'Curalidopa', not patented. The new *Curcuma* plant was discovered and selected by the Inventor as a single flowering plant within a population of plants of 'Curalidopa' in a controlled greenhouse environment in Naaldwijk, The Netherlands in June, 2016.

Asexual reproduction of the new *Curcuma* plant by axillary bud meristem culture in a controlled environment in Naaldwijk, The Netherlands since August, 2016 has shown that the unique features of this new *Curcuma* plant are stable and reproduced true to type in successive generations of asexual reproduction.

SUMMARY OF THE INVENTION

Plants of the new *Curcuma* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Curalidimp'. These characteristics in combination distinguish 'Curalidimp' as a new and distinct *Curcuma* plant:

1. Upright plant habit with slightly outwardly arching leaves.
2. Moderately vigorous to vigorous growth habit.
3. Freely clumping growth habit.
4. Relatively broad leaves.
5. Freely flowering habit.
6. Inflorescences with bright red purple-colored upper flower bracts positioned above the foliar plane on strong and erect peduncles.

Plants of the new *Curcuma* differ from plants of the mutation plant, 'Curalidopa', in the following characteristics:

1. Plants of the new *Curcuma* have larger flowers than plants of 'Curalidopa'.
2. Plants of the new *Curcuma* have more upper flower bracts than plants of 'Curalidopa'.
3. Plants of the new *Curcuma* have brighter red purple-colored upper flower bracts than plants of 'Curalidopa'.

Plants of the new *Curcuma* can also be compared to plants of *Curcuma alismatifolia* 'Curalimei', disclosed in U.S. Plant Pat. No. 25,124. In side-by-side comparisons plants of the new *Curcuma* differ from plants of 'Curalimei' in the following characteristics:

1. Plants of the new *Curcuma* are taller than plants of 'Curalimei'.
2. Plants of the new *Curcuma* are more freely clumping than plants of 'Curalimei'.
3. Leaves of plants of the new *Curcuma* are broader than leaves of plants of 'Curalimei'.
4. Plants of the new *Curcuma* have bright red purple-colored upper flower bracts whereas plants of 'Curalimei' have dark pink-colored upper flower bracts.

BRIEF DESCRIPTION OF THE PHOTOGRAPHS

The accompanying photographs illustrate the overall appearance of the new *Curcuma* plant showing the colors as true as it is reasonably possible to obtain in colored reproductions of this type. Colors in the photographs may differ slightly from the color values cited in the detailed botanical description which accurately describe the colors of the new *Curcuma* plant.

The photograph on the first sheet is a side perspective view of a typical plant of 'Curalidimp' grown in a container.

The photograph on the second sheet is a close-up view of a typical inflorescence of 'Curalidimp'.

DETAILED BOTANICAL DESCRIPTION

The aforementioned photographs and following observations and measurements describe plants grown during the early autumn in 17-cm containers in a glass-covered greenhouse in Naaldwijk, The Netherlands and under cultural practices typical of commercial *Curcuma* production. During the production of the plants, day temperatures ranged from 22° C. to 25° C., night temperatures ranged from 20° C. to 22° C. and light levels averaged 55 kilolux. Plants were 17 weeks old when the photographs and the detailed description were taken. In the following description, color references are made to The Royal Horticultural Society Colour Chart, 2015 Edition, except where general terms of ordinary dictionary significance are used.

Botanical classification: *Curcuma alismatifolia* 'Curalidimp'.

Parentage: Naturally-occurring whole plant mutation of *Curcuma alismatifolia* 'Curalidopa', not patented.

Propagation:

*Type*.—By axillary bud meristem culture.

*Time to initiate roots*.—About ten days at temperatures about 23° C.

*Time to produce a rooted young plant*.—About 28 to 30 days at temperatures about 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately branching, medium density.

Plant description:

*Plant and growth habit*.—Upright plant habit with outwardly arching leaves; overall shape, broadly obovate; freely clumping habit with about 15 basal shoots forming per plant; moderately vigorous to vigorous growth habit and moderate growth rate.

*Plant height, soil level to top of foliar plane*.—About 68.7 cm.

*Plant height, soil level to top of floral plane*.—About 81.8 cm.

*Plant diameter*.—About 62 cm.

Leaf description:

*Leaf arrangement*.—Alternate; simple.

*Length, fully expanded*.—About 30.7 cm.

*Width, fully expanded*.—About 6.8 cm.

*Shape*.—Broadly lanceolate to narrowly ovate.

*Apex*.—Long apiculate.

*Base*.—Attenuate, sheathing.

*Margin*.—Entire; unlobed.

*Venation*.—Parallel.

*Aspect*.—Initially upright, then slightly outwardly arching.

*Texture and luster, upper and lower surfaces*.—Smooth, glabrous; non-rugose; matte.

*Color*.—Developing leaves, upper surface: Close to between 143A and 144A. Developing leaves, lower surface: Close to 144A. Fully expanded leaves, upper surface: Close to 137A; midvein, close to N186C; lateral venation, close to 137B to 137C. Fully expanded leaves, lower surface: Close to NN137D; midvein, close to N138C; lateral venation, close to NN137B.

*Leaf sheaths*.—Length: About 26.8 cm. Width: About 1.7 cm. Texture and luster, upper surface: Smooth, glabrous; glossy. Texture and luster, lower surface: Smooth, glabrous; slightly glossy. Color, upper surface: Close to 145B; venation, close to 144A. Color, lower surface: Close to 145B; venation, close to 144A.

*Petioles*.—Length: About 35 cm. Diameter: About 7 mm by 10 mm. Strength: Strong. Texture and luster: Smooth, glabrous; matte. Color, upper surface: Close to 137B. Color, lower surface: Close to NN137C to NN137D.

Inflorescence description:

*Arrangement*.—Upright terminal spike inflorescences developing directly from the basal shoots with showy upper flower bracts; typically each spike with about eleven clusters each with about four flowers; about 240 flowers developing during the flowering season; flowers face mostly upright.

*Time to flower*.—In The Netherlands, plants flower from summer into autumn; flowering continuous during this period; plants begin flowering about 13 weeks after planting.

*Flower longevity*.—Flowers last about three days on the plant; flowers persistent; plants maintain good substance for about 40 days.

*Fragrance*.—Faint; somewhat spicy.

*Flower buds*.—Length: About 3.1 cm. Diameter: About 8 mm. Shape: Oblanceolate. Texture and luster: Smooth, glabrous; moderately glossy. Color: Towards the base and mid-section, close to NN155D; towards the apex, close to 85A.

*Inflorescence length*.—About 14.8 cm.

*Inflorescence diameter*.—About 7.6 cm.

*Flowers*.—Length: About 3.7 cm. Diameter: About 1.8 cm by 2.2 cm. Flower throat diameter: About 6 mm. Flower tube length: About 1.8 cm. Flower tube diameter: About 4 mm. Shape and arrangement: Zygomorphic with three petals, conspicuous labellum and two lateral corolla lobes (staminodia), fused towards the base; gamosepalous calyx with three sepals.

*Labellum*.—Length: About 2.2 cm. Width: About 1.6 cm. Shape: Spatulate; fused at the base. Apex: Emarginate. Margins: Entire; moderately undulate. Texture and luster, upper surface: Smooth, glabrous; moderately velvety; matte. Texture and luster, lower surface: Smooth, glabrous; slightly glossy. Color: When opening, upper surface: Close to 86A fading towards the center and base, close to N87B; central narrow stripe, close to 17C. When opening, lower surface: Close to 86B; towards the center and base, close to 85D. Fully opened, upper surface: Close to 86A fading towards the center and base, close to N87B; central narrow stripe, close to 17C; venation, similar to lamina colors; color becoming closer to N79C with development. Fully opened, lower surface: Close to 86B; towards the center and the base, close to 85D; venation, similar to lamina colors; color becoming closer to N79C with development.

*Lateral corolla lobes*.—Length: About 1.7 cm. Width: About 7 mm. Shape: Elliptic. Apex: Bluntly acute. Margins: Entire; not undulate. Texture and luster, upper surface: Smooth, glabrous; moderately velvety; matte. Texture and luster, lower surface: Smooth, glabrous; slightly glossy. Color: When opening and fully opened, upper surface: Close to N155A; venation, proximally, close to N155A and distally, close to 85C; color becoming closer to N79C with development. When opening and fully opened, lower surface: Close to NN155C; venation, proximally, close to NN155C and distally, close to 85D; color becoming closer to N79C with development.

*Petals*.—Length, dorsal petal: About 1.4 cm. Length, lateral petals: About 1.6 cm. Width, dorsal petal: About 9 mm. Width, lateral petals: About 6 mm. Shape, dorsal petals: Ovate. Shape, lateral petals: Narrowly oblong. Apex, dorsal and lateral petal: Bluntly acute. Margins, dorsal and lateral petals: Entire; not undulate. Texture and luster, dorsal and lateral petals, upper surface: Smooth, glabrous; matte. Texture and luster, dorsal and lateral petals, lower surface: Smooth, glabrous; moderately glossy. Color, dorsal petals: When opening and fully opened, upper surface: Close to NN155D; towards the apex, close to 85C to 85D; venation, similar to lamina colors; color does not change with development. Fully opened, upper and lower surfaces: Close to between 85C and 85D fading towards the base to close to NN155C; venation, similar to lamina colors; color does not change with development. Color, lateral petals: When opening and fully opened, upper surface: Close to NN155D; towards the apex, close to 85C to 85D; venation, similar to lamina colors; color does not change with development. Fully opened, upper and lower surfaces: Close to between 85C and 85D fading towards the base to close to NN155C; towards the apex, close to 84B; venation, similar to lamina colors; color does not change with development. Color, flower throat: Close to NN155B; venation, close to NN155B. Color, flower tube: Close to N155B; venation, close to N155B.

*Calyx*.—Length: About 4 mm. Diameter: About 3 mm. Quantity of sepals and arrangement: Three in a single whorl; fused at the base. Sepal length: About 4 mm. Sepal width: About 2.5 mm. Sepal shape: Narrowly obovate. Sepal apex: Bluntly acute. Sepal base: Broadly cuneate, fused. Sepal margin: Entire. Sepal texture and luster, upper and lower surfaces: Smooth, glabrous; moderately glossy. Sepal color: When opening and fully opened, upper surface: Close to NN155D. When opening and fully opened, lower surface: Close to NN155D.

*Upper flower bracts*.—Quantity: About nine upper bracts per inflorescence. Length: About 6.6 cm. Width: About 4.4 cm. Shape: Ovate; slightly concave. Apex: Broadly acute. Base: Cuneate. Margin: Entire; slightly undulate. Texture and luster, upper and lower surfaces: Smooth, glabrous; moderately glossy. Color: When opening and fully opened, upper surface: Close to N74C; towards the apex, close to between N186C and 200B; venation, similar to lamina. When opening and fully opened, lower surface: Close to NN74B to NN74C; towards the apex, close to 183C; venation, close to between N186C and 200B.

*Lower flower bracts*.—Quantity: About ten lower bracts per inflorescence. Length: About 3.3 cm. Width: About 3.6 cm. Shape: Broadly obovate to nearly flabellate; strongly concave. Apex: Obtuse. Base: Cuneate. Margin: Entire; undulate. Texture and luster, upper surface: Smooth, glabrous; moderately glossy. Texture and luster, lower surface: Smooth, glabrous; glossy. Color: When opening and fully opened, upper surface: Close to 145A; distally, strongly tinged with close to N77A; venation, similar to lamina. When opening and fully opened, lower surface: Close to 146D; towards the apex, close to 146B; venation, proximally, similar to lamina and distally, close to N77A.

*Peduncles*.—Length: About 63.3 cm. Diameter: About 7 mm. Strength: Strong. Aspect: Mostly erect. Texture and luster: Smooth, glabrous; matte. Color: Close to between 143B and 144A.

*Stamens*.—Quantity: Two per flower; fused. Filament length: About 7 mm. Filament diameter: About 4 mm. Filament color: Close to NN155D. Anther length: About 8 mm. Anther width: About 2 mm. Anther shape: Narrowly oblong. Anther color: Close to 156C to 156D; apex, close to 84A. Pollen amount: Moderate. Pollen color: Close to 155C.

*Pistils*.—Quantity per flower: One. Pistil length: About 2.8 cm. Style length: About 2.6 cm. Style color: Close to NN155D. Stigma diameter: About 2 mm. Stigma shape: Cupped. Stigma color: Close to 85D. Ovary color: Close to 150D.

*Seeds and fruits*.—To date, seed and fruit development have not been observed on plants of the new *Curcuma*.

Pathogen & pest resistance: To date, plants of the new *Curcuma* have not been observed to be resistant to pathogens or pests common to *Curcuma* plants.

Temperature tolerance: Plants of the new *Curcuma* have been observed to be tolerant to temperatures ranging from about 5° C. to about 40° C. and are suitable for USDA Hardiness Zones 10 to 12.

It is claimed:

1. A new and distinct *Curcuma* plant named 'Curalidimp' as illustrated and described.

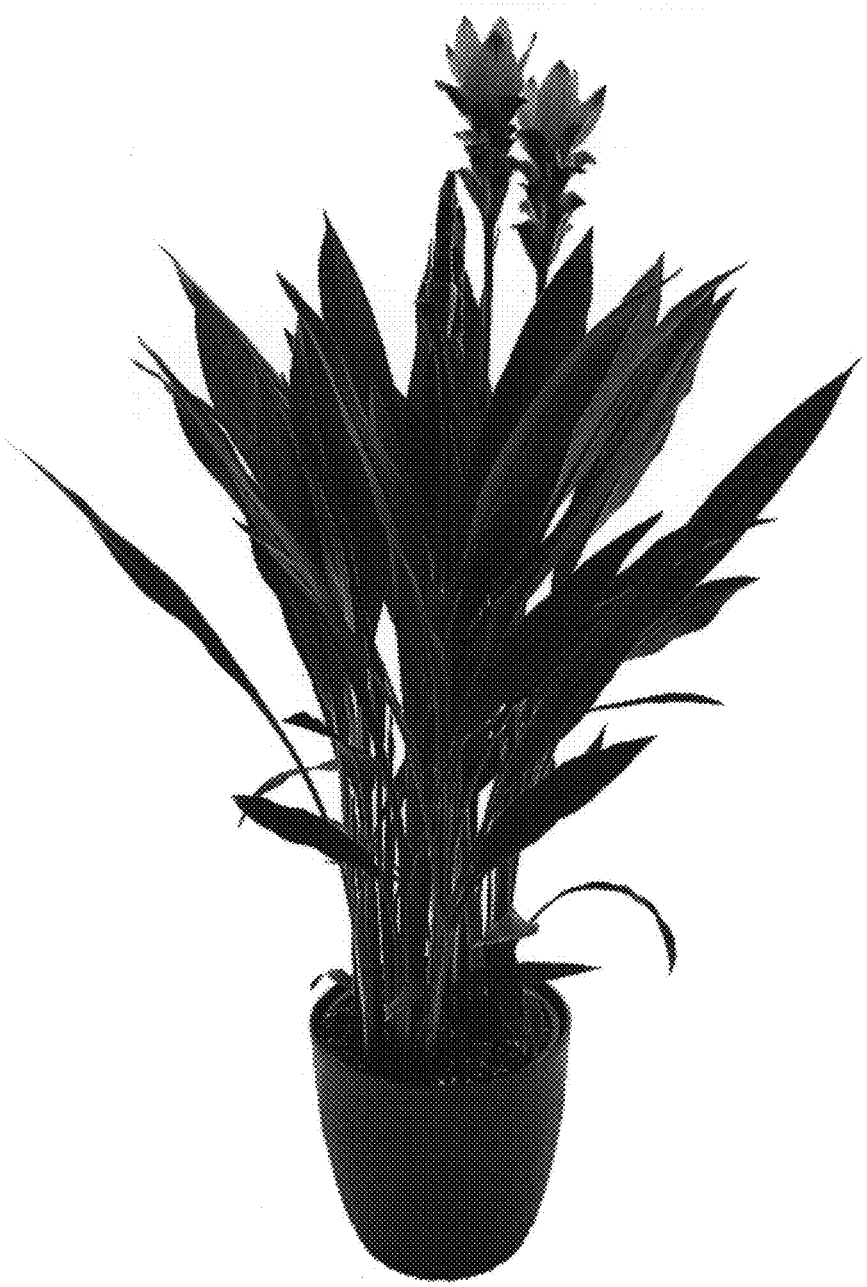

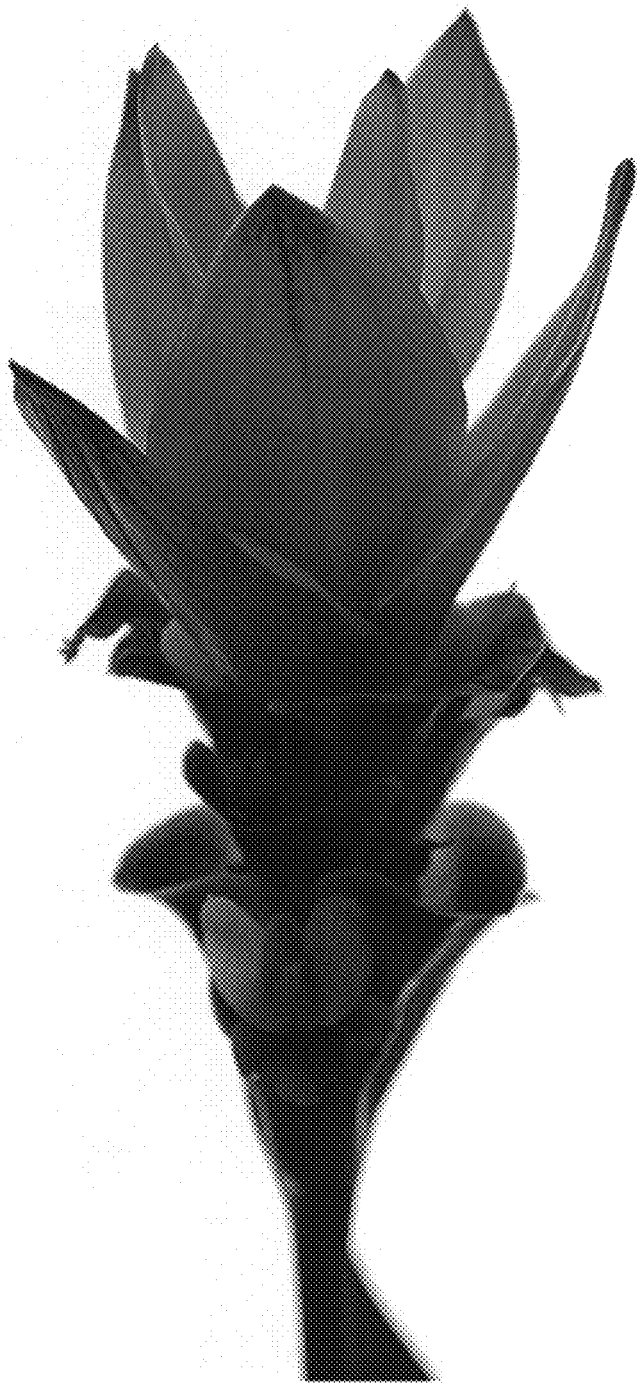

* * * * *